United States Patent
Kwon et al.

(10) Patent No.: US 11,058,298 B2
(45) Date of Patent: Jul. 13, 2021

(54) POLARIZATION FUNDUS CAMERA FOR EFFECTIVELY SUPPRESSING INTERNAL REFLECTION

(71) Applicant: AIINSIGHT INC., Busan (KR)

(72) Inventors: Han Jo Kwon, Busan (KR); Keun Heung Park, Busan (KR)

(73) Assignee: AIINSIGHT INC., Busan (KR)

( * ) Notice: Subject to any disclaimer, the term of this patent is extended or adjusted under 35 U.S.C. 154(b) by 202 days.

(21) Appl. No.: 16/470,482

(22) PCT Filed: Jul. 6, 2018

(86) PCT No.: PCT/KR2018/007692
§ 371 (c)(1),
(2) Date: Jun. 17, 2019

(87) PCT Pub. No.: WO2019/009660
PCT Pub. Date: Jan. 10, 2019

(65) Prior Publication Data
US 2019/0313901 A1  Oct. 17, 2019

(30) Foreign Application Priority Data

Jul. 7, 2017 (KR) .................. 10-2017-0086208
Jul. 17, 2017 (KR) .................. 10-2017-0090275

(51) Int. Cl.
*A61B 3/12* (2006.01)
*A61B 3/11* (2006.01)
(Continued)

(52) U.S. Cl.
CPC ............ *A61B 3/112* (2013.01); *A61B 3/0008* (2013.01); *A61B 3/14* (2013.01); *G02B 27/28* (2013.01)

(58) Field of Classification Search
CPC ........... A61B 3/12; A61B 3/0008; A61B 3/14; A61B 3/156; A61B 5/00; G02B 27/28; G02B 27/0018; G02B 27/283
See application file for complete search history.

(56) References Cited

U.S. PATENT DOCUMENTS 7,798,642 B2 * 9/2010 Itoh ..................... A61B 3/14
351/206
10,575,730 B2   3/2020 Li
(Continued)

FOREIGN PATENT DOCUMENTS

CN    106388765 A    2/2017
JP    2007-029726 A  2/2007
(Continued)

OTHER PUBLICATIONS

International Search Report for PCT/KR2018/007692 dated Oct. 5, 2018 from Korean Intellectual Property Office.
(Continued)

*Primary Examiner* — Mohammed A Hasan
(74) *Attorney, Agent, or Firm* — Paratus Law Group, PLLC

(57) ABSTRACT

Disclosed is a polarization fundus camera including: an illumination unit emitting light; a diffusion lens; an illumination lens irradiating the light introduced from the diffusion lens; a mirror reflecting light introduced from the illumination lens; a polarization beam splitter; an objective lens enlarging an image of a fundus formed by the light introduced from the polarization beam splitter; a short-range eyepiece lens reducing an image of the fundus enlarged by the objective lens; a linear polarization filter; a narrowband optical filter; and an imaging device.

13 Claims, 12 Drawing Sheets

(51) Int. Cl.
*A61B 3/00* (2006.01)
*A61B 3/14* (2006.01)
*G02B 27/28* (2006.01)

(56) References Cited

U.S. PATENT DOCUMENTS

2006/0146284 A1 7/2006 Collins et al.
2015/0002817 A1* 1/2015 Alasaarela ............... A61B 3/12
                                                      351/208
2016/0296112 A1* 10/2016 Fletcher .................. A61B 3/14

FOREIGN PATENT DOCUMENTS

| | | |
|---|---|---|
| JP | 2008-110202 A | 5/2008 |
| JP | 2017-512992 A | 5/2017 |
| KR | 10-2013-0099113 A | 9/2013 |
| KR | 10-2015-0136977 A | 12/2015 |
| WO | WO 99/62397 A1 | 12/1999 |

OTHER PUBLICATIONS

Extended European Search Report for related EP application No. 18828888.0 dated Feb. 16, 2021 from European Patent Office.
Indian Examination Report for related IN application No. 201927041367 dated Feb. 24, 2021 from Indian Patent Office.

* cited by examiner

POLARIZATION FUNDUS CAMERA FOR EFFECTIVELY SUPPRESSING INTERNAL REFLECTION

CROSS-REFERENCE TO PRIOR APPLICATIONS

This application is a National Stage Patent Application of PCT International Patent Application No. PCT/KR2018/007692 filed on Jul. 6, 2018 under 35 U.S.C. § 371, which claims priority to Korean Patent Application Nos. 10-2017-0086208 filed on Jul. 7, 2017 and 10-2017-0090275 filed on Jul. 17, 2017, which are all hereby incorporated by reference in their entirety.

BACKGROUND

The present invention is a type of fundus camera which is one of eye examination and diagnosis equipment. A conventional color fundus camera is equipment for illuminating retinas with light of a visible band (400 to 640 nm), and then showing retinal lesions and diagnosing retinal diseases. However, the present invention relates to a choroidal imaging fundus camera capable of photographing both a choroidal vessel and a choroidal lesion at the back of the retina with near-infrared rays having a wavelength longer than 640 nm and a device comprising the same.

A conventional fundus camera primarily uses a technique of imaging a fundus through a light source of a visible ray band and photographing a reflected fundus shade into an image recording device. Such a method is still widely used today, but many diseases involving choroidal vessels and choroidal capillaries, such as senile AMD, hereditary macular degeneration, infectious or noninfectious, and choroiditis, which are difficult to identify with conventional techniques, have recently been identified and the number of patients is also increasing.

In order to obtain images of choroidal vessels and lesions, the light source must pass through a retinal pigment epithelium containing a melanin pigment through a transparent retina. However, the melanin pigment absorbs light in a visible light band so that the melanin pigment looks dark on its own, and is an obstacle to obtaining the images of the choroidal vessels and the choroidal lesions. In addition, there is a macular pigment in the maculae that absorbs short wavelengths of the cyanite series, and it is difficult to identify the choroidal vessels and lesions by imaging the visible light band.

Currently, the most commonly used indocyanine green fluorescence angiography equipment is used to identify the choroidal vessels and lesions in clinical practice. The device us an image recording device recording near-infrared light having a longer wavelength, which injects an indocyanine green pigment into a vein, images a near-infrared light source near 800 nm to the fundus, and absorbs and emits the near-infrared light from indocyanine green pigment circulating in the choroids. However, such a device has the following disadvantages because the device images the choroid by using a light source of 800 nm or more.

(i) The light source is expensive. The reason is that since the light source of the near-infrared light is generally used only in a special measuring equipment, the light source is low in demand. (ii) An optical design for allowing the near-infrared light is required and coating is required to absorb or reflect the near-infrared light in order to avoid reflection from a cornear and a leans constituting an eyeball and this also expensive. (iii) Most of all, there are few used imaging device capable shooting the near-infrared light with a high resolution and even a near-infrared light imaging device with a low resolution is very expensive. Consequently, the equipment can be owned by larger hospitals and many patients are being diagnosed and treated for the diseases in secondary or tertiary hospitals. Therefore, an object of the present invention is to photograph clear choroidal vessels and lesions at low cost and acquire a choroidal fundus photograph by overcoming three disadvantages mentioned above.

SUMMARY

The present invention is contrived to solve the problem and an object of the present invention is to image a choroid using 650 to 700 nm near infrared light and obtain a clear choroidal image.

Further, according to the present invention, since an optical design permitting expensive near-infrared rays is not required, the manufacturing cost can be reduced.

Further, an object of the present invention is to increase and facilitate the diagnostic value of the choroidal fundus camera and facilitate diagnosis and treatment of the disease by increasing the clearness of the image by using the narrowband optical filter.

Further, according to the present invention, various types of reflections can be removed and clear fundus photographs with high light transmissibility can be obtained by using a combination of the polarization beam splitter and the linear polarization filter in the fundus camera using the homonymous illumination.

Further, according to the present invention, an illumination is provided on a plane portion where the retina is not distributed in the eyes of a human or an animal and a sclera around the plane portion, thereby capturing a wide range of fundus photographs by suppressing the axial motion without causing the pupil reflex.

In addition, the present invention can provide fundus photographs to a medical staff which can acquire a wide range of fundus photographs at a low cost and have more diagnostic value.

The technical objects of the present invention are not limited to the aforementioned technical objects, and other technical objects, which are not mentioned above, will be apparently appreciated by a person having ordinary skill in the art from the following description.

According to the present invention, a polarization fundus camera for effectively suppressing internal reflection includes: an illumination unit 10 emitting light; a diffusion lens diffusing light introduced from the illumination unit 10; an illumination lens irradiating the light introduced from the diffusion lens 20 at a predetermined emission angle; a mirror 40 reflecting light introduced from the illumination lens 30; a polarization beam splitter 50 transmitting P polarized light and reflecting S polarized light from the light introduced from the mirror 40; an objective lens 60 enlarging an image of a fundus formed by the light introduced from the polarization beam splitter 50; a short-range eyepiece lens 70 reducing an image of the fundus enlarged by the objective lens 60; a linear polarization filter 80 through which only the P polarized light passes; a narrowband optical filter 90 having a band of 12 nm or less for the light passing through the linear polarization filter and filtering the light emitted from the polarization beam splitter 50; and an imaging device 100 acquiring an image by converting the light passing through the narrowband optical filter 90 into an electric signal, in which the linear polarization filter 80 includes each of a first linear polarization filter 81 provided between the illumination unit 10 and the polarization beam splitter 50, and a second linear polarization filter 82 provided between the polarization beam splitter 50 and the short-range eyepiece lens 70.

By the technical solution, according to the preset invention, the clear choroidal image can be obtained by imaging the choroid using 650 to 700 nm near infrared light.

Further, according to the present invention, since an optical design permitting expensive near-infrared rays is not required, the manufacturing cost can be reduced and the medical treatment cost can be reduced.

Further, according to the present invention, by increasing the clearness of the image by using the narrowband optical filter, the diagnostic value of the choroidal fundus camera is increased and diagnosis and treatment of the disease are facilitated.

Further, according to the present invention, various types of internal reflections can be removed and clear fundus photographs can be obtained by using a combination of the polarization beam splitter and the linear polarization filter in the fundus camera using the homonymous illumination.

In addition, the present invention can be applied to both mydriatic and non-mydriatic fundus cameras and can be applied to both the homonymous illumination fundus camera and the non-homonymous illumination fundus camera, and as a result, good compatibility can be obtained.

Further, according to the present invention, by acquiring noise-free fundus photographs by the non-mydriatic fundus camera in a short period of time, it is possible to reduce the side effects and reduce the cost of medical care by reducing the use of the mydriatic fundus camera.

Further, according to the present invention, the present invention can be effectively used for an ophthalmologic examination and the non-mydriatic fundus camera because the fundus can be effectively photographed at a wide angle without using an expensive optical device or an expensive laser-based fundus imaging device.

In addition, the present invention can be usefully used in fundus photographing in an animal fundus photography or in a child in which it is difficult to cooperate.

Further, the present invention can be applied to all devices that acquire a wider range of fundus photographs without irradiating light directly to the pupil and indirectly irradiating the light through the plane portion to cause no pupil contraction.

DETAILED DESCRIPTION

The present invention is a type of fundus camera which is one of eye examination and diagnosis equipment. A conventional color fundus camera is equipment for illuminating retinas with light of a visible band (400 to 640 nm), and then showing retinal lesions and diagnosing retinal diseases. However, the present invention relates to a choroidal imaging fundus camera capable of photographing both a choroidal vessel and a choroidal lesion at the back of the retina with near-infrared rays having a wavelength longer than 640 nm and a device comprising the same.

Specific matters including problems to be solved for the present invention, a solving means of the problems, and the effect of the invention for the present invention are included in exemplary embodiments and drawings to be described below. Advantages and/or features of the present invention, and a method for achieving the advantages and/or features will become obvious with reference to embodiments to be described below in detail together with the accompanying drawings.

Figure 1:
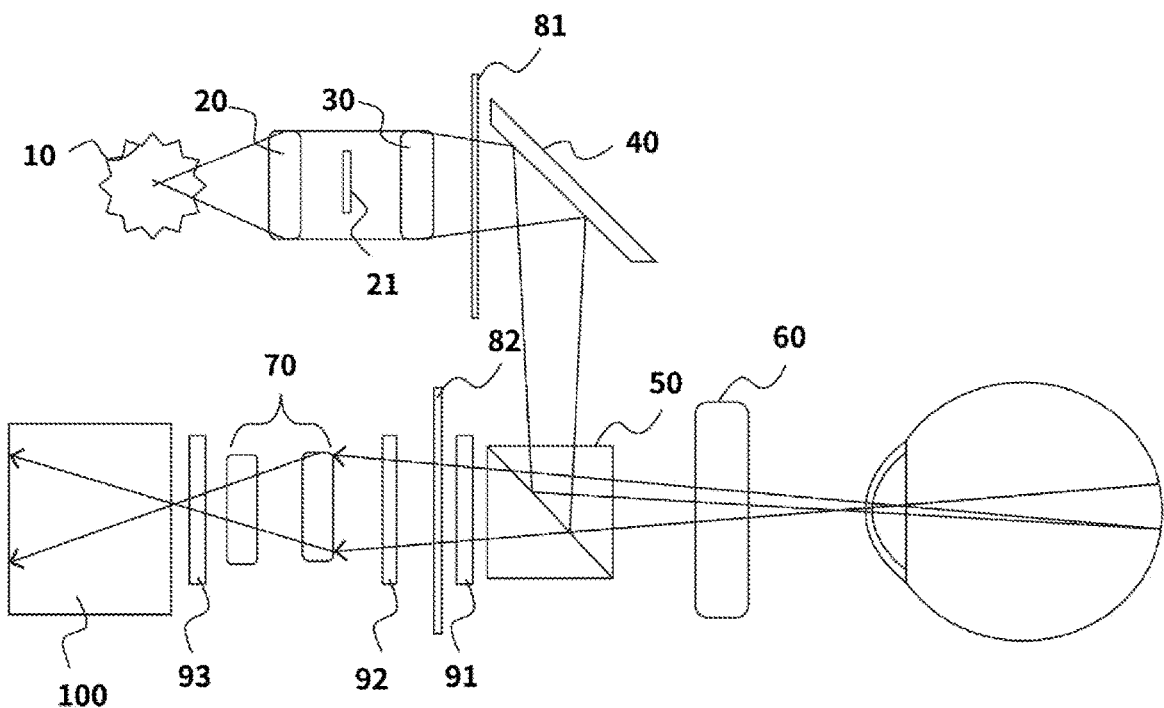
FIG. 1 is a view illustrating a polarization fundus camera for effectively suppressing internal reflection of the present invention.

As illustrated in FIG. 1, a polarization fundus camera for effectively suppressing internal reflection of the present invention includes an illumination unit 10, a diffusion lens 20, an illumination lens 30, a mirror 40, a polarization beam splitter 50, an objective lens 60, a short-range eyepiece lens 70, a linear polarization filter 80, a narrowband optical filter 90, and an imaging device 100.

First, the illumination unit 10 is preferably a white light emitting diode, but a near infrared light emitting diode, a xenon lamp, or a laser may also be used as a light source.

Figure 5:
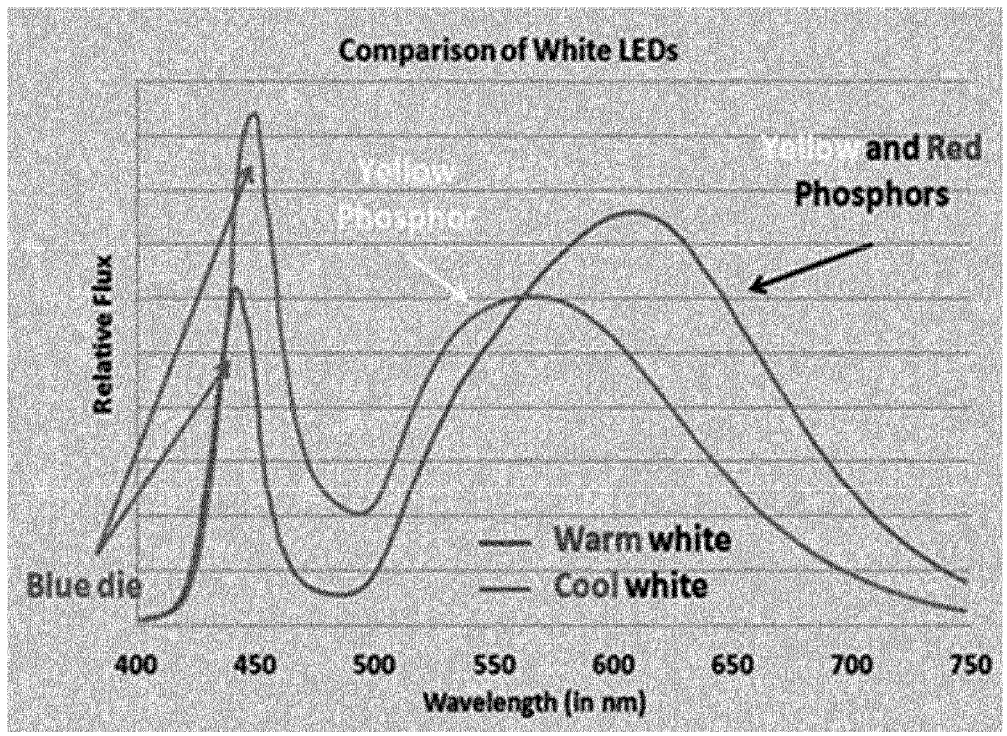
FIG. 5 is a graph illustrating a spectrum of a white light emitting diode.

More specifically, as illustrated in FIG. 5, the white light emitting diode is divided into a warm white light emitting diode and a cold white light emitting diode, and both the white light emitting diodes emit near infrared rays of 650 to 700 nm. Particularly, since the warm white light emitting diode emits energy twice larger than that of the cool white light emitting diode in a band of 650 to 700 nm, the illumination unit 10 is suitable as a light source of the warm white light emitting diode.

Also, the illumination unit 10 may use a visible light-emitting diode for fundus photographing, and may use a light-emitting diode having an emission spectrum in the range of 700 to 1000 nm for near-infrared fundus photographing. In addition, all kinds of light emitting diodes such as light emitting diodes having emission lines in a narrow spectrum region of 450 to 500 nm or 700 to 800 nm may be used for fluorescence fundus photographing.

Figure 8:
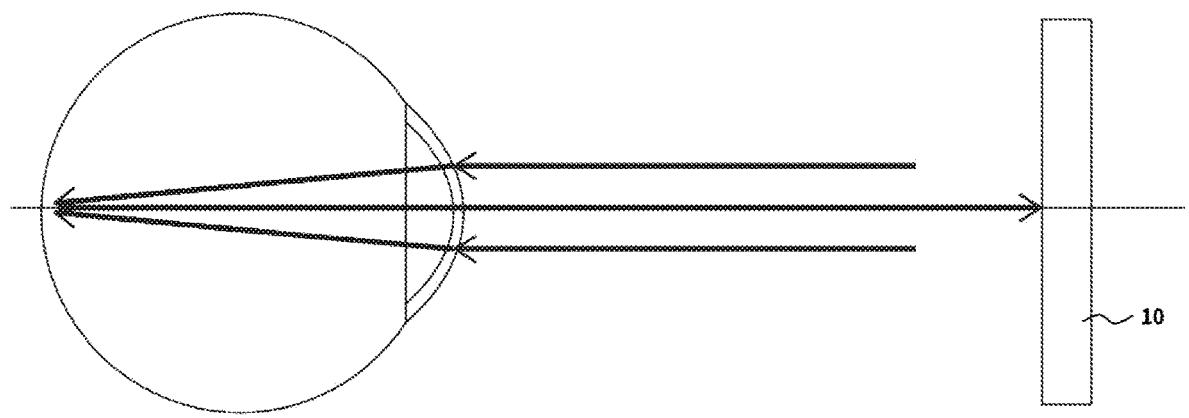
FIG. 8 is a view illustrating a principle of a conventional illumination device 11 through the pupil.

In general, the fundus camera is a technique for illuminating a plane portion, which is an anatomical position of the eyeball away by 2 to 4 mm from the limbus, which is the boundary between the cornea and the sclera. As illustrated in FIG. 8, the fundus camera used in the ophthalmologic examination photographs a fundus within a viewing angle of 50° and radiates bright light through a pupil, and as a result, a narrow range of retina is imaged due to pupilary reflex, and a maximum viewing angle that can be photographed becomes narrow.

Figure 7:
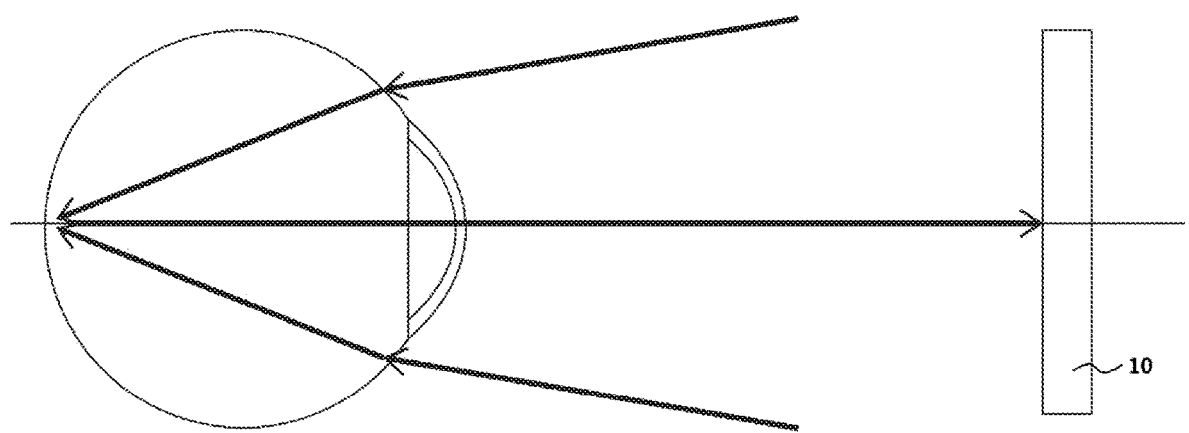
FIG. 7 is a view illustrating a principle of an illumination device through a planar imaging according to the present invention.

On the other hand, according to a retinnography method of the present invention, as illustrated in FIG. 7, an illumination is provided on a planar portion where the retina is not distributed in a human or animal eye and a sclera around the planar portion, to capture a wide range of fundus photographs by suppressing the myosis without causing the pupilary reflex.

Figure 10:
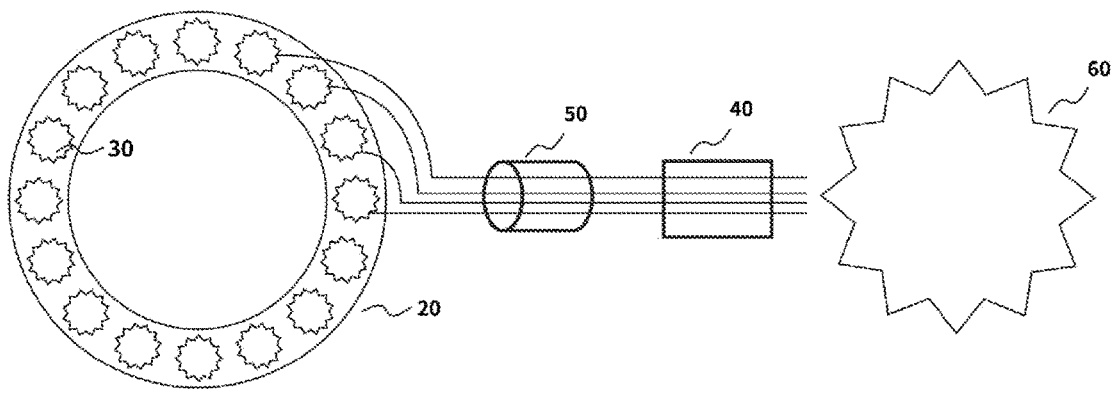
FIG. 10 is a view illustrating an optical fiber-based optical transmission method according to the present invention.
Figure 11:
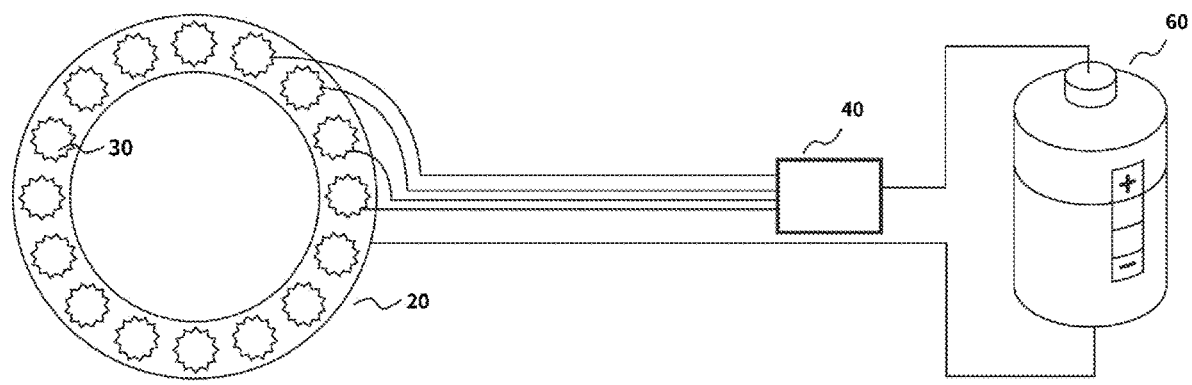
FIG. 11 is a view illustrating an optical fiber-based optical transmission method according to the present invention.

As illustrated in FIGS. 10 to 11, the illumination unit 10 includes an illumination device 11 based on an optical fiber 14a or a light emitting diode 14b, a light source 15 for supplying light to the illumination device 11, a control unit 12 for controlling the illumination device 11, and a power supply unit 13 for supplying power of the light to the light source 15.

First, the illumination device 11 is provided with the lighting device 11 based on the optical fiber 14a (FIG. 10) or the light emitting diode 14b (FIG. 11), and is provided with a disk-shaped substrate or a fixing device.

Figure 9:
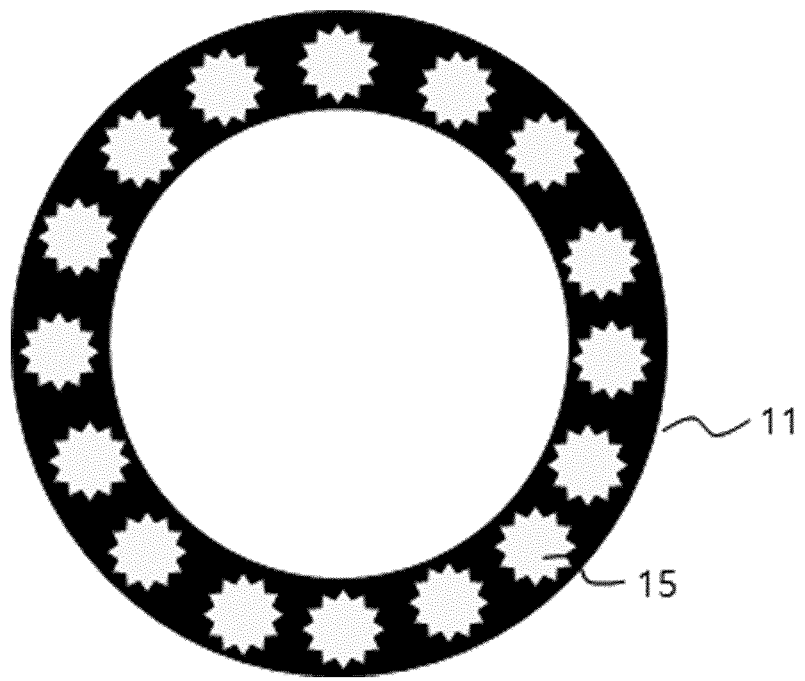
FIG. 9 is a view illustrating an illumination device based on an optical fiber or a light emitting diode according to the present invention.

As illustrated in FIG. 9, it is preferable that the illumination device 11 is provided with a disk-shaped substrate having an inner diameter of 7 to 9 mm at the center and an outer diameter of 9 to 11 mm at the center. An efficient planar imaging to be designed is possible as the condition.

More specifically, when the inner diameter of the illumination device 11 is less than 7 mm from the center, there is a problem that the light transmittance is reduced into the vitreous body and the retina due to an illumination with a corrugated wrinkle portion having many melanin pigments and a thick structure. When the inner diameter of the illumination device 11 is more than 9 mm from the center, there is a problem that the illumination device 11 is not accurately imaged on the plane portion of the eyeball, which is a space where the divergent light is absorbed, the light transmittance is decreased, and a brighter light source is required to increase power consumption, and there is a problem that as the length of the arc of the illumination device increases, more light sources are required and manufacturing cost is increased.

Further, when the outer diameter of the illuminating device 11 is less than 9 mm from the center, the light emitted from the illuminating device 11 may not be accurately imaged on a planar portion of the eyeball and when the outer diameter of the illumination device 11 exceeds 11 mm from the center, the light may be directly illuminated to the peripheral retina to cause a pupil contraction, and phototoxicity may occur in the peripheral retina illuminated when used for a long time. Therefore, it is preferable to manufacture the illumination device 11 under the above conditions.

Next, the light source 15 supplies light to the illumination device 11 and may be provided with a lens connected to the end of the optical fiber 14a, the end itself of the optical fiber 14a, or the light emitting diode 14b.

In addition, the light emitted from the light source 15 may be infrared light of 1300 to 650 nm and visible light of 650 to 400 nm.

As illustrated in FIG. 7, the light emitted from the light source 15 is scattered in the sclera, and goes straight on the vitreous cavity of the eyeball to illuminate the retina, and the illuminated light again enters the fundus camera 10 or the detector, which is an imaging sensor, through the pupil. The fundus photograph is obtained through the process of entering the detector. In addition, the light source 15 can be used not only for fundus photography but also for autofluorescence fundus photography and funduscopic angiography.

The light source 15 may be arranged in the form of a circular array in the illumination device 11. As illustrated in FIG. 5, in the case of the pars plana illumination based on the optical fiber 14a, the light source 15 may be disposed with a higher degree of integration so that more efficient illumination can be performed and light having various spectra may be irradiated at a time.

In the case of the pars plana illumination based on the light emitting diode 14b, the light source 15 may be implemented by a surface mount device type or a double in-line package type light emitting diode 14b and a light emitting diode 14b combined with a lens.

Next, the control unit 12 may adjust the light source 15 of the illumination device 11 to 360° around the cornea and block the illumination supply or control the light source 15 to 180° or 30°. In addition, the control unit 12 may adjust the brightness of the light source 15, and control the illumination to be turned on or off in a particular location.

Next, the power supply unit 13 provides power of the light to the light source 15.

Specifically, in the pars plana illumination based on the optical fiber 14a, as illustrated in FIG. 11, the power supply unit 13 may use general Xenon light and use high-brightness LEDs of various wavelengths, and can also use a laser if necessary.

In addition, in the pars plana illumination based on the light emitting diode 14b, the power supply unit 13 can be used in combination with a general DC power source or a used battery as illustrated in FIG. 11.

More specifically, as illustrated in FIGS. 10 to 11, the illumination device 11 may be manufactured by largely dividing an optical fiber 14a type light transmission method and a light emitting diode 14b type light transmission method.

First, as illustrated in FIG. 10, when the light is transmitted to the light source 15, the optical fiber 14a type light transmission method is provided with at least one selected from a method of distributing a plurality of optical fibers 14a around the circular array after transmitting light to a single number of optical fiber 14a and a method of connecting the entirety of the optical fibers 14a dispersed to the plurality of optical fibers 14a to the power supply unit 13 provided with the xenon light or the light emitting diode 14b.

In the method for distributing a single number of optical fiber to a plurality of optical fibers, the single optical fiber may be distributed to a plurality of channels of optical fibers by using a fanout patch cord, and each of the distributed channels may insert an optical filter through an optical adapter or illuminate the pars plana through an optical device at the end.

Further, in the optical fiber 14*a* type light transmission method, the control unit 12 is provided between the single optical fiber 14*a* and the power supply unit 13 in the form of an optical filter or a light blocking filter to transmit light of a specific wavelength or to control or block the intensity of the light.

Next, in the light emitting diode 14*b* type light transmission method, when the light is transmitted to the light source 15, the light emitting diode 14*b* is disposed on the top of a PCB substrate and then a wire or a flexible PCB substrate is connected with the power supply unit 13 of any one selected from a DC power supply or a battery.

In addition, in the light emitting diode 14*b* type light transmission method, the control unit 12 is provided as a current circuit including a diode, a transistor, and a controller so as to turn on or off the light emitting diode 14*b* at a specific position.

Next, the diffusing lens 20 diffuses the light introduced from the illumination unit 10. The diffusing lens 20 includes a central cover 21, which may adjust the light.

Figure 18:
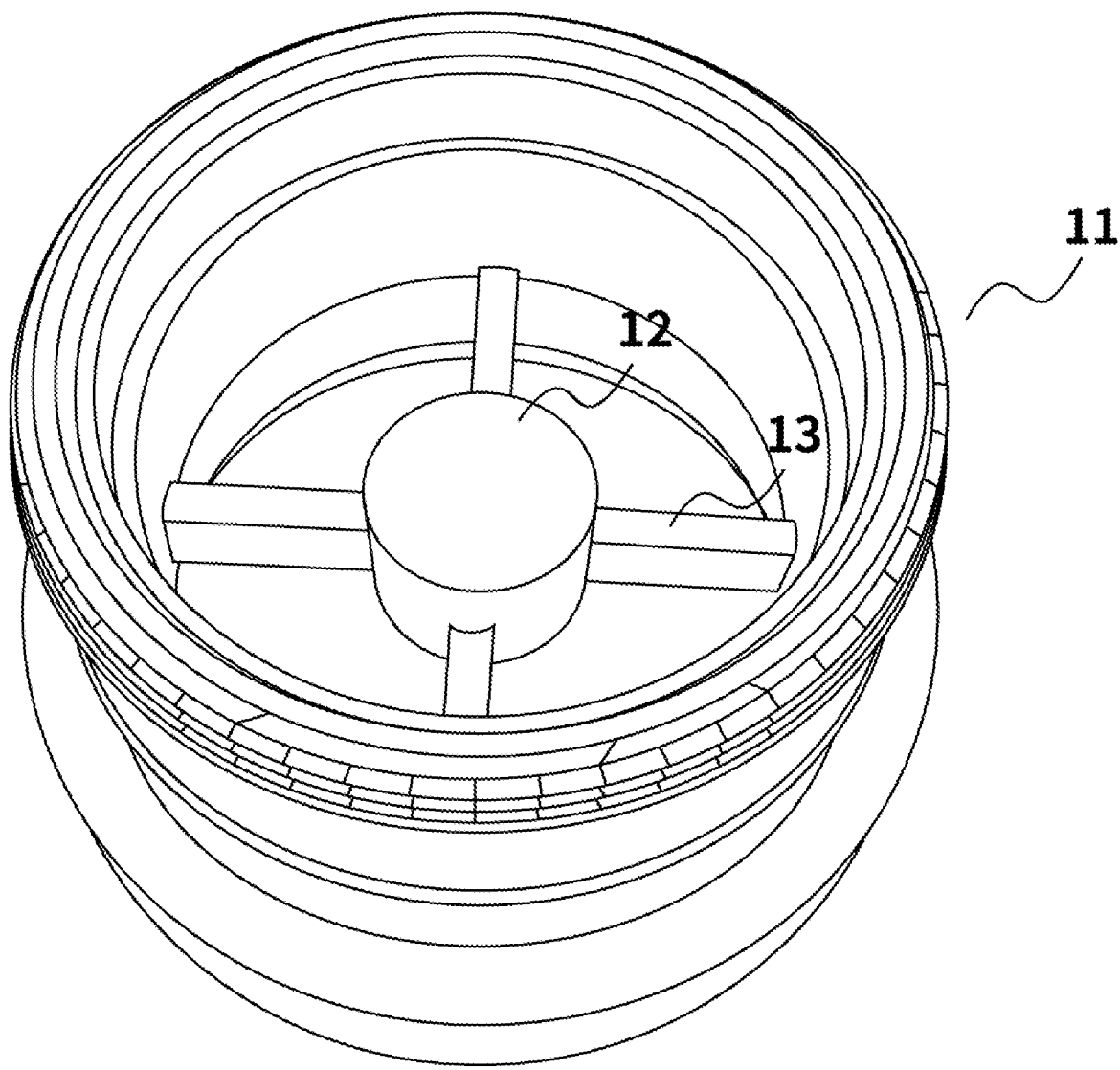
FIG. 18 is a view illustrating a masking structure 22 that may be used instead of a central cover 21.

The central cover 21 is a device for reducing the light incident to the c center to minimize corneal reflex. A minimum size of the central cover 21 varies depending on the focal length of the objective lens 60, but is generally 2.0 to 5.0 mm, and the central cover 21 is a core device that prevents illumination from being incident on the periphery of a peak convex surface of the central part of the cornea. The central cover 21 may be stuck on the front surface or the back surface of the diffusion lens 20 in a sticky manner and may be marked on the central part of the diffusion lens 20 by an oil or water pen, and as illustrated in FIG. 18, the central portion may be blocked by the masking structure 22.

The masking structure 22 includes a central mask 23 and a spider part 24 for supporting the central mask 23. The spider part 24 may be designed variously so that the number of blades is 1 to 4, and as the number of blades of the spider part 24 increases, the stability increases, but there is a problem that a light amount decreases and a diffraction image is generated. In order to reduce the diffraction image, the spider part 24 may be implemented in a curved shape.

Next, the illumination lens 30 irradiates the light introduced from the diffusion lens 20 at a predetermined emission angle. The light introduced from the diffusion lens 20 is taken out more clearly and uniformly by the illumination lens 30.

Next, the mirror 40 reflects the light introduced from the illumination unit 30. The light introduced from the illumination unit 30 is taken out to a polarization beam splitter 50 to be described below by changing a direction of the light.

The mirror 40 is a structure required for positioning the illumination on the same side as the camera, and does not affect the optical performance of the fundus camera.

The mirror 40 is not required when the illumination is arranged perpendicular to the camera. In the case where the illumination unit 10 includes one or more illumination units including visible light and near-infrared light, two lights having different properties may be incident on the polarization beam splitter 50 using one beam splitter and two different illumination units 10 instead of the mirror 40.

Next, the polarization beam splitter 50 transmits P-polarized light and reflects S-polarized light from the light introduced from the mirror 40.

Figure 3:
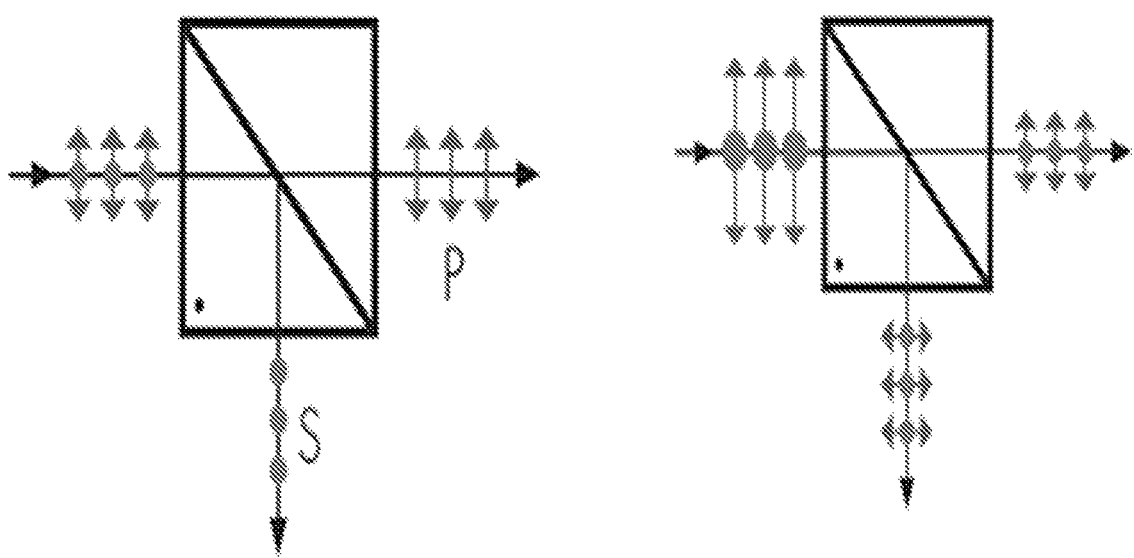
FIG. 3 is a view illustrating a principle of a polarizing beam splitter and a principle of a non-polarizing beam splitter.

More specifically, as illustrated in FIG. 3A, all the light sources 15 include a light source 15 corresponding to P-polarized light and a light source 15 corresponding to S-polarized light, and in the light source 15, the light corresponding to the P-polarized light passes through the beam splitter 50, and the light corresponding to the S-polarized light is reflected by a 90° bent portion of the optical axis. On the other hand, as illustrated in FIG. 3B, the same principle as the polarization beam splitter 50 is not applied to the non-polarized beam splitter.

The polarization beam splitter 50 may be made of a very thin film material or a single square, rectangular, or circular glass material, and can use a rectangular parallelepiped polarization beam splitter 50 in which two prisms are combined. Particularly, the rectangular parallelepiped polarization beam splitter 50 in which two prisms are combined is advantageous in that a clear image can be obtained because the light that is refracted on the interface and then incident on the optical axis again is small.

Next, the linear polarization filter 80 is linearly formed, and filters the P-polarized light to be transmitted. More specifically, it is preferable that the linear polarization filter 80 is provided in a direction perpendicular to the P-polarized light so that the most P-polarized light is transmitted and only the light deflected to the pure P-polarized light is transmitted.

The linear polarization filter 80 is provided as a first linear polarization filter 81 and a second linear polarization filter 82, respectively.

The first linear polarization filter 81 is provided between the illumination unit 10 and the polarization beam splitter 50. As the first linear polarizing filter 81 is closer to the illumination unit 10, the size of the first linear polarizing filter 81 may be reduced and the overall cost of the fundus camera manufactured according to the present invention may be reduced.

As illustrated in FIG. 1, the first linear polarization filter 81 may be provided between the illumination lens 30 and the mirror 40. When the first linear polarization filter 81 is provided between the illumination lens 30 and the mirror 40, the first linear polarization filter 81 is installed in a direction parallel to the illumination lens 30 so as to allow the most P-polarized light to be transmitted.

The first linear polarization filter 81 may be provided between the mirror 40 and the polarization beam splitter 50 (not illustrated). When the first linear polarization filter 81 is provided between the mirror 40 and the polarization beam splitter 50, the first linear polarization filter 81 is installed in a direction vertical to the illumination lens 30 so as to allow the most P-polarized light to be transmitted.

The second linear polarization filter 82 is provided between the polarization beam splitter 50 and the short-range eyepiece lens 70. As the second linear polarization filter 82 is further away from the polarization beam splitter 50, the size of the second linear polarizing filter 82 may be reduced, but as the distance increases, it is disadvantageous that the overall optical path of the fundus camera manufactured by the present invention increases. The second linear polarization filter 82 may be disposed directly behind the polarization beam splitter 50 or directly in front of the imaging sensor of the camera.

A method of minimizing the size of the linear polarization filter 80 is to attach the linear polarization filter 80 to directly the front surface of the imaging sensor included in the camera by the size of the image sensor. For example, when the size of the imaging sensor is 1 inch, the linear polarization filter 80 may use a diameter of 1 inch, and when the size of the imaging sensor is ½ inch, the linear polarization filter 80 may use a diameter of ½ inch.

In FIG. 3A, as illustrated in the principle of the polarization beam splitter 50, when the first linear polarization filter 81 is positioned in front of the polarization beam splitter 50 and then positioned to transmit only the light corresponding to the P-polarized light, the largest amount of light is irradiated to the retina, and when the first linear polarization filter 81 is positioned to transmit only the light corresponding to the S-polarized light, the light irradiated to the retina is blocked. Therefore, the first linear polarization filter 81 is a device for adjusting the amount of light, and at the same time, serves to irradiate only the pure P-polarized light to the fundus.

When the P-polarized light passing through the polarization beam splitter 50 is reflected by an optical medium in front of the polarization beam splitter 50 and returns, when the light is reflected, the P-polarized light is changed into S-polarized light by a principle that when the light is reflected, the phase is changed to 180° and the P-polarized light is changed to S-polarized light. The light changed into the S-polarized light is reflected by the polarization beam splitter 50 at all 90° and can not enter the detector. Similarly, while diffuse reflection occurs in various paths in the optical medium, fundus, a part of the light source 15 irradiated with P-polarized light is reflected by S-polarized light and a part is reflected by P-polarized light so that only the P-polarized light passes through the polarization beam splitter 50.

The P-polarized light having passed through the polarization beam splitter 50 passes through the second linear polarization filter 82, so that only the P-polarized retina image of high purity is transmitted to the detector, and noises caused by various reflections may be blocked at a high removal rate.

In other words, it is preferable that the first linear polarization filter 81 and the second linear polarization filter 82 have the same polarity and transmit only P-polarized light of high purity. By the definition of the high purity, the removal rate of the light that is orthogonal to the first linear polarization filter 81 and the second linear polarization filter 82 is less than about 0.1% (<1/1000) so that the reflection shade disappears from the fundus photograph. This is because most CCD or CMOS cameras have an ADC resolution of 12 bits and should have a removal rate of less than 1/1024 in order to reduce the error to a measurement error of 1 bit for digital image processing. For this purpose, when manufacturing the present invention, it is necessary to check that angular distortion between the two linear polarization filters 80 and the polarization beam splitter 50 is within 2 to 6 rad (about 1.8°) before a product.

The linear polarization filter 80 may also be made of a very thin film material, and a square or rectangular glass material. It is advantageous in that the film material is thin in thickness and low in cost, but the film material is easy to bend, so that the optical properties of the entire fundus camera may be changed, and it is disadvantageous in that the film material is deformed or damaged by heat, but it is advantageous that the cost is low.

Next, the objective lens 60 enlarges the image formed inside the fundus after the light input from the polarization beam splitter 50 is introduced into the fundus.

Next, the short-range eyepiece lens 70 reduces the image of the funds enlarged by the objective lens 60, and as a result, the user confirms the image of the fundus.

Next, the narrowband optical filter 90 filters light having a band of 12 nm or less and a center wavelength of 650 to 700 nm from the light which passes through the linear polarization filter 80. The reason why the band of the narrowband optical filter 90 is made to 12 nm or less is that since a bandwidth of a commercial narrowband optical filter is 12 nm or less, the narrowband optical filter 90 may be purchased with low cost and since the width of the band is smaller, a chromatic aberration is reduced, an image with high clarity may be acquired and background noise may be reduced. As the bandwidth is reduced, a higher-resolution and clearer image may be obtained, but energy of transmitted light is reduced, so that a light source 15 having a higher output and a longer exposure time is required and the resolution may be degraded by image overlapping due to spontaneous movement of the eyeball for a longer exposure time. More preferably, in general, in consideration of a fundus photograph exposure time of 0.005 sec to 0.020 sec, it is appropriate that the narrowband optical filter 90 has a bandwidth of 4.5 nm to 12.0 nm.

Figure 2:
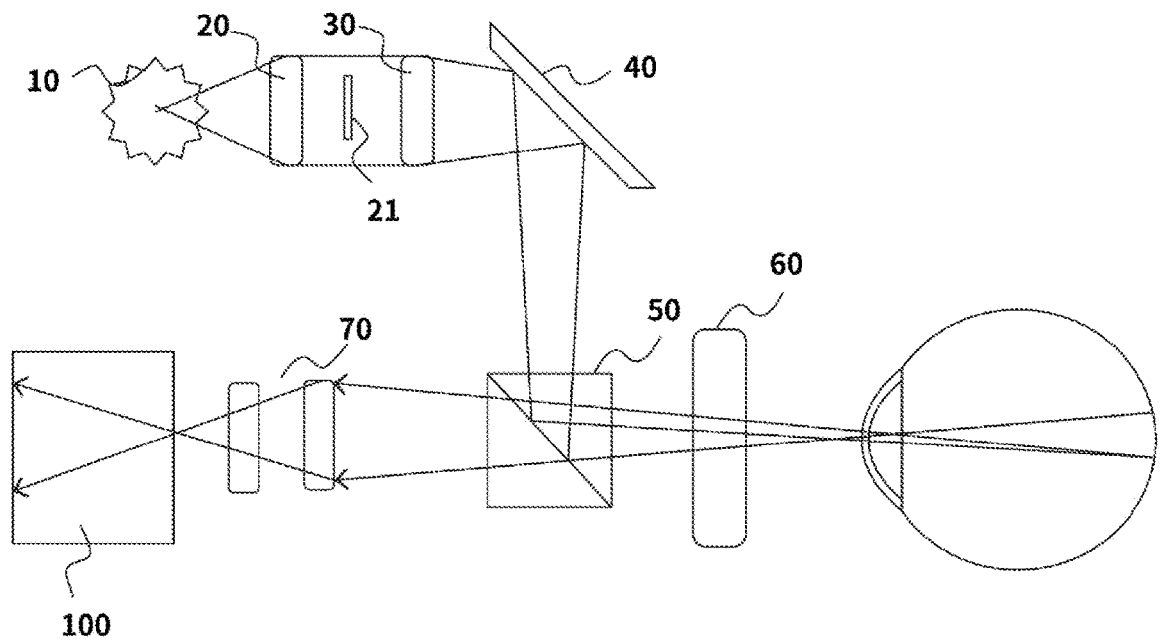
FIG. 2 is a view illustrating a basic configuration of a general homonymous illumination fundus camera.

Like the configuration of FIG. 2, a fundus camera constituted by the polarization beam splitter 50 without the narrowband optical filter 90 and the two linear polarization filters 80 may remove various noise reflected on a portion other than the retina and photograph a clear retina image, but when the narrowband optical filter 90 is added, it is possible to more clearly image the choroid by transmitting retinal pigment epithelium through the light source 15 including the near-infrared light of 650 to 700 nm.

Figure 4:
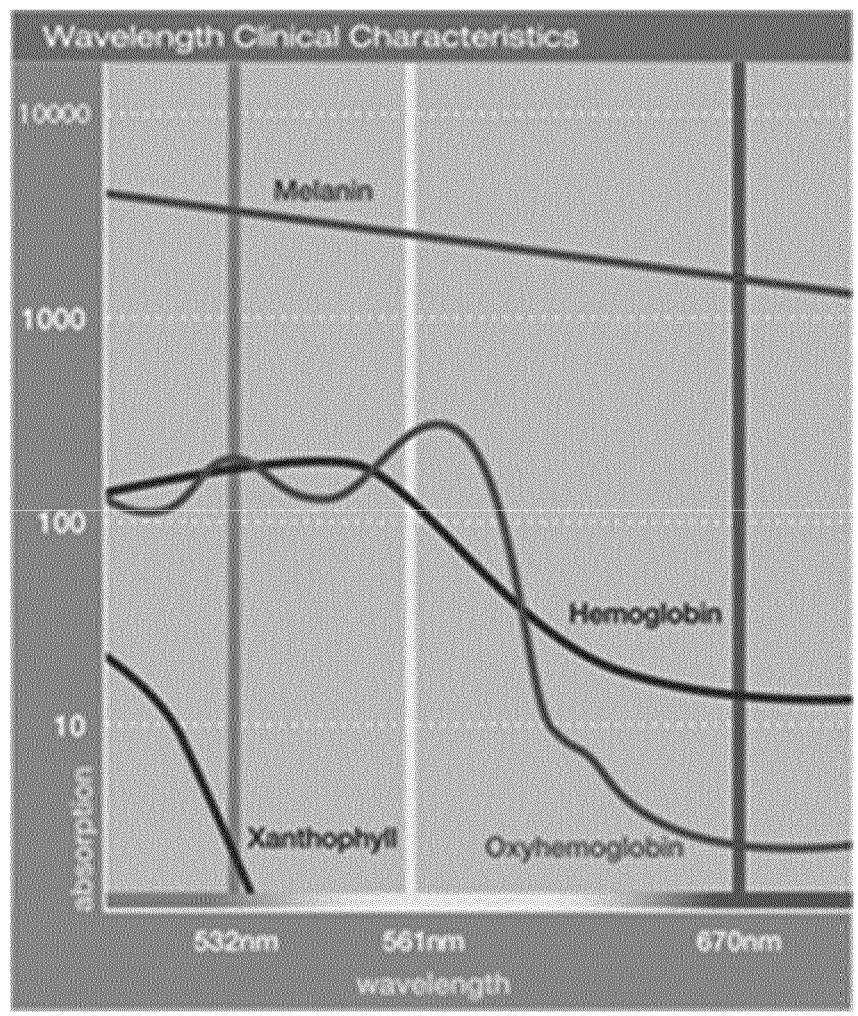
FIG. 4 is a graph illustrating absorption rates of a macular pigment and a retinal pigment epithelium in a visible-near infrared region.

More specifically, as described in the Background of the Invention, since the choroidal membrane contains a melanin pigment that absorbs light in a visible light band and a macular pigmentary tissue that absorbs a short wavelength of a cyanite series, it is difficult to acquire the images of the choroidal vessels and lesions. In FIG. 4, it can be seen that most cyanite visible light having a short wavelength is absorbed by the macular pigment with an absorption rate for a visible light-near-infrared band wavelength of the macular pigment which exists in the retinal pigment epithelium and the macular which is the center of the retina and visible light in yellow and red bands is absorbed by the retinal pigment epithelium and as the visible light moves to the near-infrared region, the absorption rates in the two pigments are reduced.

The narrowband optical filter 90 is constituted by a first narrowband optical filter 91, a second narrowband optical filter 92, and a third narrowband optical filter 93. The narrowband optical filter 90 may be provided anywhere between the polarization beam splitter 50 and the imaging device 100. Since the chromatic aberration is generated due to a difference in refractive index depending on the wavelength of light generated by the illumination unit 10, it is preferable to reduce generated noise by transmitting the light through only a spectrum with a small width by using the narrowband optical filter 90. The narrowband optical filter 90 may be selected and provided as at least one of the first narrowband optical filter 91, the second narrowband optical filter 92, and the third narrowband optical filter 93 and may include all of the three filters.

First, the first narrowband optical filter 91 is provided between the polarization beam splitter 50 and the second linear polarization filter 82. The first narrowband optical filter 91 is provided between the polarization beam splitter 50 and the second linear polarization filter 82 to attach the second linear polarization filter 82 to the narrowband optical filter 90 in a film form.

The second narrowband optical filter 82 is provided between the second linear polarization filter 82 and the short-range eyepiece lens 70. The second narrowband optical filter 92 is provided between the second linear polarization filter 82 and the short-range eyepiece lens 70 and inserts various types of narrowband optical filters to acquire images in various wavelength bands.

The third narrowband optical filter 93 is provided between the short-range eyepiece lens 70 and the imaging device 100. The third narrowband optical filter 92 is provided between the short-range eyepiece lens 70 and the imaging device 100 to minimize optical interference between the narrowband optical filter 90 and the imaging device 100.

Next, the imaging device 100 converts the light passing through the narrowband optical filter 90 into an electric signal to acquire a photographed image. The imaging device 100 may sensitively receive the near infrared light source 15 of 650 to 700 nm. More preferably, the imaging device 100 may use an analog type charge coupled device or a metal oxide semiconductor.

Figure 6:
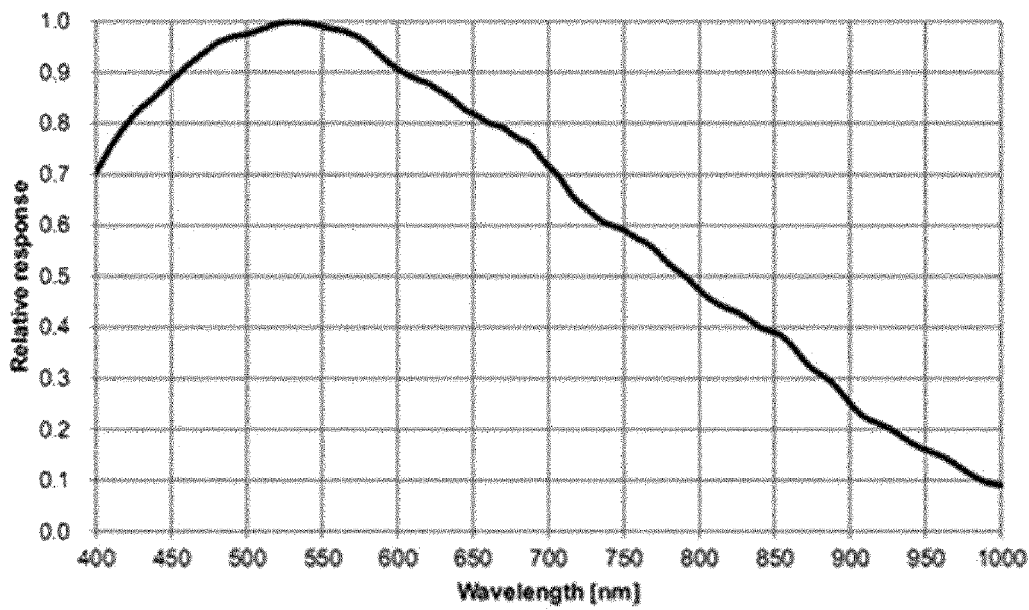
FIG. 6 is a graph illustrating photon efficiency of a monochrome imaging device 100.

As illustrated in FIG. 6, in the case of photon efficiency of the imaging device 100, photon efficiency of light having a wavelength longer than 700 nm is drastically reduced. When the fundus is illuminated with an illumination in a band in which the photon efficiency is drastically reduced, a more exposure time is required and eyes of a person persistently moves, which may becomes an obstacle in acquiring cleaner choroidal vessels or lesions and the retina is irradiated with a light source 15 with stronger energy, thereby damaging the retina.

The polarization fundus camera for effectively suppressing the internal reflection according to the present invention may image the choroid by transmitting the retinal pigment epithelium and the macular pigment by using a light source 15 having a near-infrared emission spectrum or a visible light emission spectrum and the imaging device 100 with an absorption spectrum through the illumination unit 10 and acquire the choroidal image through the imaged choroid.

When a white light emitting diode is used as the light source 15, strong visible light is emitted, and as a result, an optical filter is required, which blocks the visible light on a front-end optical path of the imaging device 100. More specifically, the chromatic aberration is shown due to the difference in refractive index depending on the wavelength in most optical devices and a near infrared region of 650 to 700 nm is not exceptional. Accordingly, as a wavelength range of a transmission band to be irradiated is larger, more aberrations may occur and as the wavelength range is smaller, an optical aberration may be reduced and a clearer image may be obtained.

In other words, as a transmission bandwidth of the optical filter is smaller, an aberration of an optical system is smaller, a very clear image may be obtained. Therefore, the narrowband optical filter 90 may be positioned anywhere at a front side of the imaging device 100 from a rear side of the polarization beam splitter 50.

In the following description, a problem of a general fundus camera is intended to be checked by using FIGS. 15 and 16.

A. Configuration of General Homonymous Illumination Fundus Camera

Figure 15:
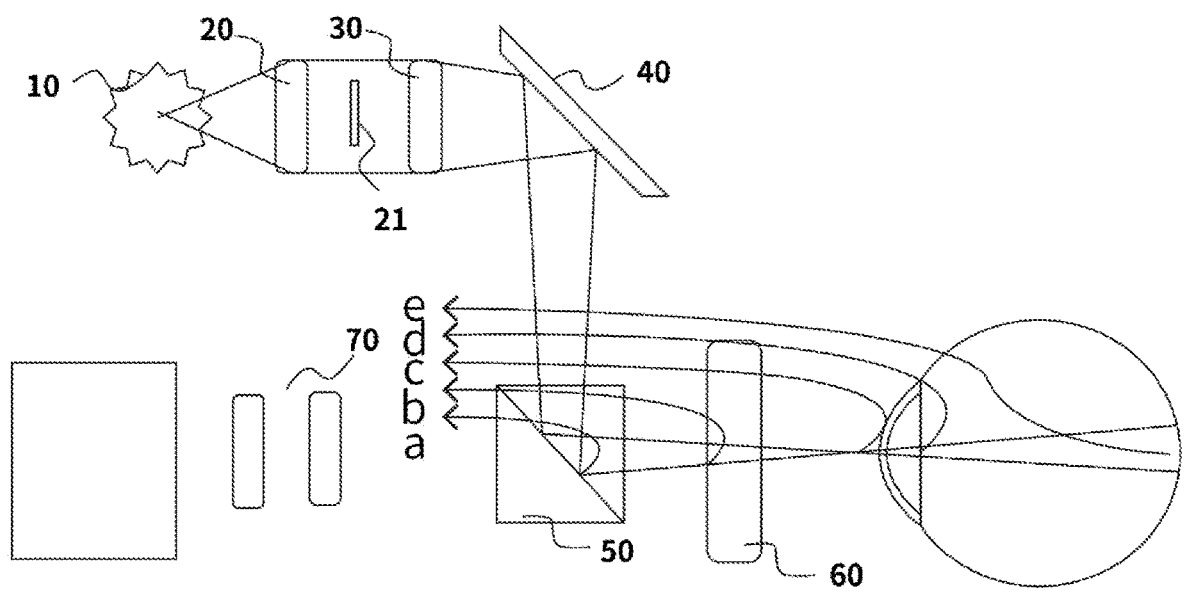
FIG. 15 is a view illustrating configurations of a conventional fundus camera and optical noises a to e generated by each configuration.
Figure 16:
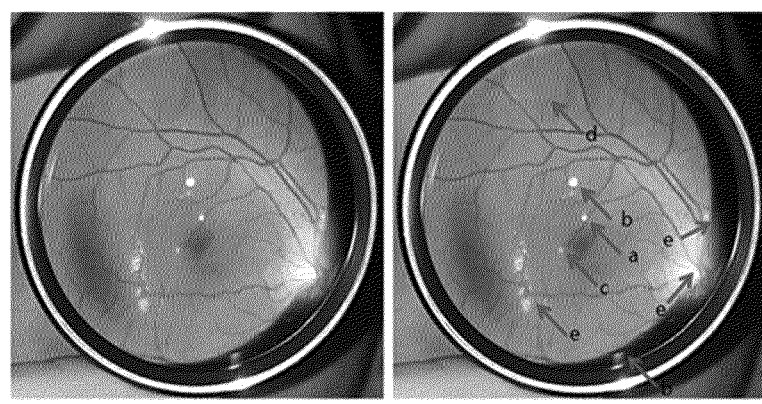
FIG. 16 is a photograph illustrating optical noises shown when the fundus is photographed by the device of FIG. 15 and marks a to e shown that the optical noises are shown from any configuration of FIG. 15.

FIG. 15 illustrates a basic configuration of a general homonymous illumination fundus camera. As illustrated in FIG. 15, the polarization beam splitter 50 is a core device that allows the images of an illumination for imaging the fundus and the imaged fundus to exist on the same axis. However, in the existing homonymous illumination fundus camera, a lot of light is lost while passing through the polarization beam splitter 50 and optical noise due to various reflections generated inside is input into a detector without filtering.

B. Various Optical Reflections Generated by General Homonymous Illumination Fundus Camera In FIG. 15, a red arrow indicates a cause and a problem of various reflections which may be generated in the general homonymous illumination fundus camera. Arrow a represents a reflection generated in the polarization beam splitter 50 and arrow b represents a reflection by the objective lens 60. Arrow c represents a reflection generated in the cornea. Arrow d represents a reflection generated in the lens. Arrow e represents a total reflection generated in a vitreous and the retina. Due to the reflections of a to e, when the fundus photograph is taken, various reflection patterns are shown, a lot of confusion occurs in confirming the fundus of the patient by a doctor. In addition, when transmissivity to transmissibility of the polarization beam splitter 50 is 50%, only half of optical energy supplied from the polarization beam splitter 50 is transferred to the fundus and only half of light transferred from the fundus is transferred to the detector.

C. Fundus Photograph taken by Using General Homonymous Illumination Fundus Camera FIG. 16 illustrates a fundus photograph taken by using the general homonymous illumination fundus camera and a substance of the reflection represented by the arrow of FIG. 15 may be confirmed by the photograph. Similarly to FIG. 16, arrow a represents the reflection generated in the polarization beam splitter 50 and arrow b represents the reflection by the objective lens 60. Arrow c represents the reflection generated in the cornea. Arrow d represents the reflection generated in the lens. Arrow e represents the total reflection generated in the vitreous and the retina. In the case of the reflections represented by the a to e, when a position of an eye of the patient or angles of the optical system and a visual axis are changed, patterns of the reflections are unpredictably changed, and as a result, the reflection may not be removed by software, thereby degrading a diagnostic value of the equipment.

D. Fundus Photograph taken by Using Choroidal Imaging Polarization Fundus Camera Using Narrowband Optical Filter according to Present Invention Hereinbelow, the choroidal imaging polarization fundus camera using the narrowband optical filter manufactured by the present invention is actually implemented and illustrated in FIG. 12 and the choroidal photograph is taken by using the present invention and illustrated in FIG. 17.

Figure 12:
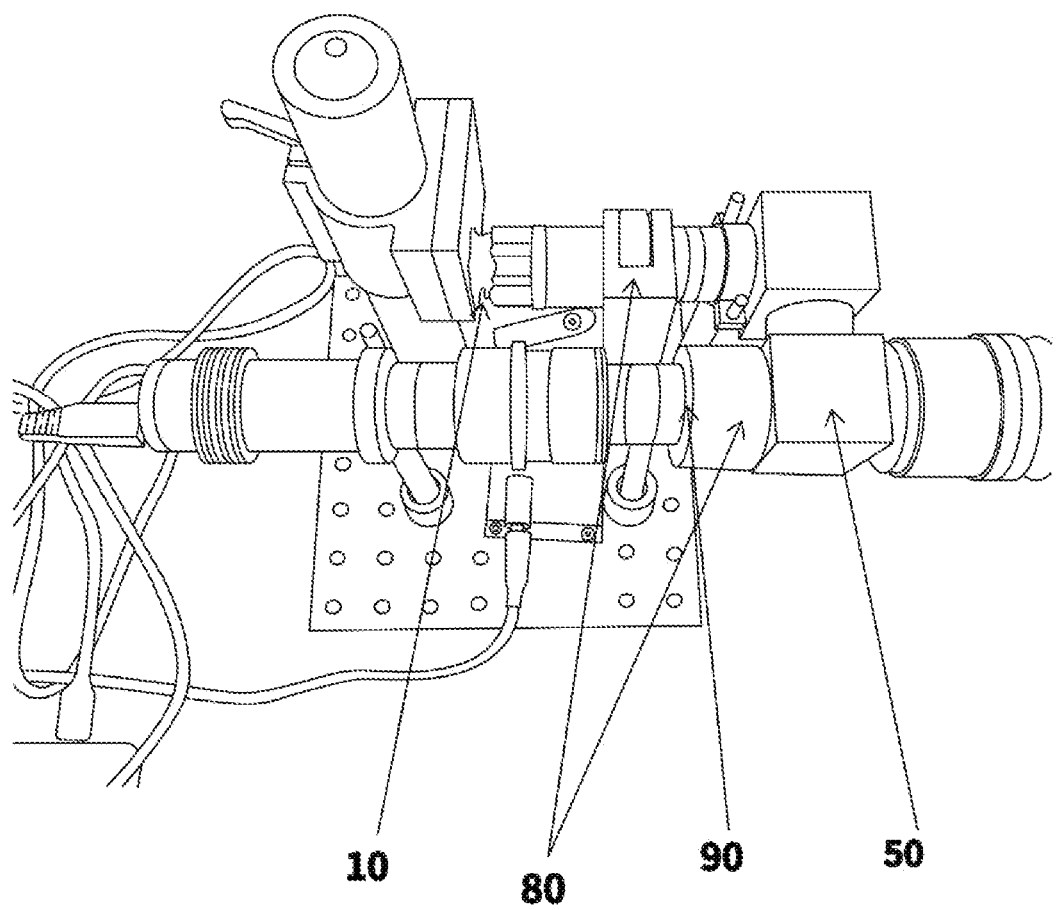
FIG. 12 is a photograph illustrating a choroidal imaging polarization fundus camera using a narrowband optical filter according to the present invention.

First, as illustrated in FIG. 12, in the choroidal imaging polarization fundus camera using the narrowband optical filter manufactured by the present invention, as the illumination unit 10, a warm white light emitting diode is used and a clear choroidal image may be obtained and manufacturing cost may be significantly reduced by using the near-infrared light of 650 to 700 nm as well as the visible light by means of the narrow optical filter 90.

Figure 17:
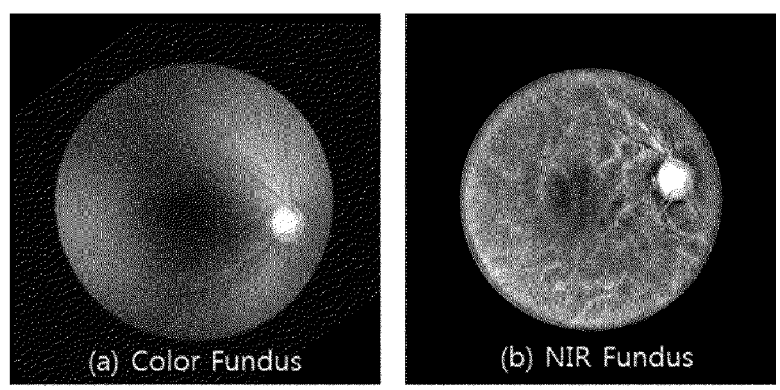
FIG. 17 is a photograph illustrating a comparison of a color choroidal photograph (a) taken after excluding the narrowband optical filter 90 and a choroid photograph (b) produced by the present invention.

FIG. 17 is the choroid imaging fundus photograph take by using the device of FIG. 12, and FIG. 17(*a*) is a photograph when the narrowband optical filter is not provided and FIG. 17(*b*) is a photograph when the narrowband optical filter 90 is provided.

When the narrowband optical filter 90 is not provided as illustrated in FIG. 17(*a*), a color fundus photograph may be taken. As illustrated in FIG. 17(*b*), when the photograph is taken by the fundus camera with the narrowband optical filter 90, the choroidal vessels which are not clearly shown in the color fundus photograph (FIG. 17(*a*)) is photographed by passing through the retinal pigment epithelium and the macular pigment to effectively photograph the choroidal vessels and lesions. Further, it can be confirmed that the noise illustrated in FIG. 16 is removed.

Figure 13:
FIG. 13 is a photograph of a fundus in a range of 55° using the fundus camera manufactured according to the present invention.
Figure 14:
FIG. 14 is a photograph of a fundus in a range of 70° using the fundus camera manufactured according to the present invention.

Further, as illustrated in FIGS. 13 and 14, the fundus camera manufactured by the present invention may set the range of the fundus which may be imaged by using various objective lenses 60 and acquire a fundus photograph without the total reflection by means of the fundus camera.

FIG. 13 is a fundus photograph actually taken by the fundus camera according to the present invention and FIG. 14 is a fundus photograph in a range of 70°. Through FIGS. 13 and 14, it can be seen that a position of a sufficient range may be photographed in photographing the fundus for the purpose of evaluating most of the retinal diseases or health examination. Further, as compared with FIG. 13, it can be seen that various types of reflection patterns shown in the general homonymous illumination fundus camera are not shown.

By the technical solution, according to the preset invention, the clear choroidal image can be obtained by imaging the choroid using 650 to 700 nm near infrared light. Further, according to the present invention, since an optical design permitting expensive near-infrared rays is not required, the manufacturing cost can be reduced and the medical treatment cost can be reduced. Further, according to the present invention, by increasing the clearness of the image by using the narrowband optical filter, the diagnostic value of the choroidal fundus camera is increased and diagnosis and treatment of the disease are facilitated. Further, according to the present invention, various types of reflections can be removed and clear fundus photographs with high light transmissibility can be obtained by using a combination of the polarization beam splitter and the linear polarization filter in the fundus camera using the homonymous illumination. Further, according to the present invention, an illumination is provided on a plane portion where the retina is not distributed in the eyes of a human or an animal and a sclera around the plane portion, thereby capturing a wide range of fundus photographs by suppressing the axial motion without causing the pupil reflex. In addition, the present invention can provide fundus photographs to a medical staff which can acquire a wide range of fundus photographs at a low cost and have more diagnostic value.

As described above, those skilled in the art will be able to understand that a technical configuration of the present invention can be easily executed in other detailed forms without changing the technical spirit or an essential feature thereof.

Therefore, the embodiments described as above are exemplary in all aspects and should be understood as not being restrictive and the scope of the present disclosure is represented by claims to be described below rather than the detailed description, and it is to be interpreted that the meaning and scope of the claims and all the changes or modified forms derived from the equivalents thereof come within the scope of the present invention.

The invention claimed is:

1. A polarization fundus camera for effectively suppressing internal reflection, comprising:
    an illumination unit emitting light;
    a diffusion lens diffusing light introduced from the illumination unit;
    an illumination lens irradiating the light introduced from the diffusion lens at a predetermined emission angle;
    a mirror reflecting light introduced from the illumination lens;
    a polarization beam splitter transmitting P polarized light and reflecting S polarized light from the light introduced from the mirror;
    an objective lens enlarging an image of a fundus formed by the light introduced from the polarization beam splitter;
    a short-range eyepiece lens reducing an image of the fundus enlarged by the objective lens;
    a linear polarization filter through which only the P polarized light passes;
    a narrowband optical filter having a band of 12 nm or less for the light passing through the linear polarization filter and filtering the light emitted from the polarization beam splitter; and
    an imaging device acquiring an image by converting the light passing through the narrowband optical filter into an electric signal,
    wherein the linear polarization filter includes each of
    a first linear polarization filter provided between the illumination unit and the polarization beam splitter, and
    a second linear polarization filter provided between the polarization beam splitter and the short-range eyepiece lens.

2. The polarization fundus camera for effectively suppressing internal reflection of claim 1, wherein the narrow optical filter is provided by a first narrowband optical filter provided between the polarization beam splitter and the second linear polarization filter.

3. The polarization fundus camera for effectively suppressing internal reflection of claim 1, wherein the narrow optical filter is provided by a second narrowband optical filter provided between the second linear polarization filter and the short-range eyepiece lens.

4. The polarization fundus camera for effectively suppressing internal reflection of claim 1, wherein the narrow optical filter is provided by a third narrowband optical filter provided between the short-range eyepiece lens and the imaging device.

5. The polarization fundus camera for effectively suppressing internal reflection of claim 2, wherein all of the first narrowband optical filter, the second narrowband optical filter, and the third narrowband optical filter are provided.

6. The polarization fundus camera for effectively suppressing internal reflection of claim 1, wherein the first linear polarization filter and the second linear polarization filter have the same polarity.

7. The polarization fundus camera for effectively suppressing internal reflection of claim 1, wherein the illumination unit includes
    an illumination device based on an optical fiber and receiving the light from the illumination unit,
    a control unit adjusting a light source of the illumination device to 360° around the cornea and blocking the illumination supply or controlling the light source to 180° or 30°, and
    a power supply unit providing power of the light to the illumination unit, to perform pars plana illumination, and
    the pas planar illumination is performed at a distance away from the limbus.

8. The polarization fundus camera for effectively suppressing internal reflection of claim 7, wherein in the pas planar illumination,
    the illumination units are arranged in a planar circular array of the illumination device, and
    the circular array is provided by a disk-shaped substrate.

9. The polarization fundus camera for effectively suppressing internal reflection of claim 8, wherein the optical fiber based illumination device is provided any selected one of, at the time of transferring the light to the illumination unit, a scheme of transferring the light to a single optical fiber and dispersing the light to multiple optical fibers around the circular array, and a scheme of connecting all of the multiple dispersed optical fibers to the power supply unit provided as a zenon light or light emitting diode.

10. The polarization fundus camera for effectively suppressing internal reflection of claim 7, wherein the optical fiber based illumination device is provided in such a manner that the control unit is provided in an optical filter type between the single optical fiber and the power supply unit to transfer light of a specific wavelength or adjust or block an intensity of the light.

11. The polarization fundus camera for effectively suppressing internal reflection of claim 7, wherein the light emitting diode based illumination device is provided in such a manner that, at the time of transferring the light to the illumination unit, the light emitting diode is disposed on the top of a PCB substrate and then a wire or a flexible PCB substrate is connected with the power supply unit of any one selected from a DC power supply or a battery.

12. The polarization fundus camera for effectively suppressing internal reflection of claim 3, wherein all of the first narrowband optical filter, the second narrowband optical filter, and the third narrowband optical filter are provided.

13. The polarization fundus camera for effectively suppressing internal reflection of claim 4, wherein all of the first narrowband optical filter, the second narrowband optical filter, and the third narrowband optical filter are provided.

* * * * *